May 16, 1967 E. S. BOERNER Plant Pat. 2,740
CHRYSANTHEMUM PLANT
Filed May 11, 1966
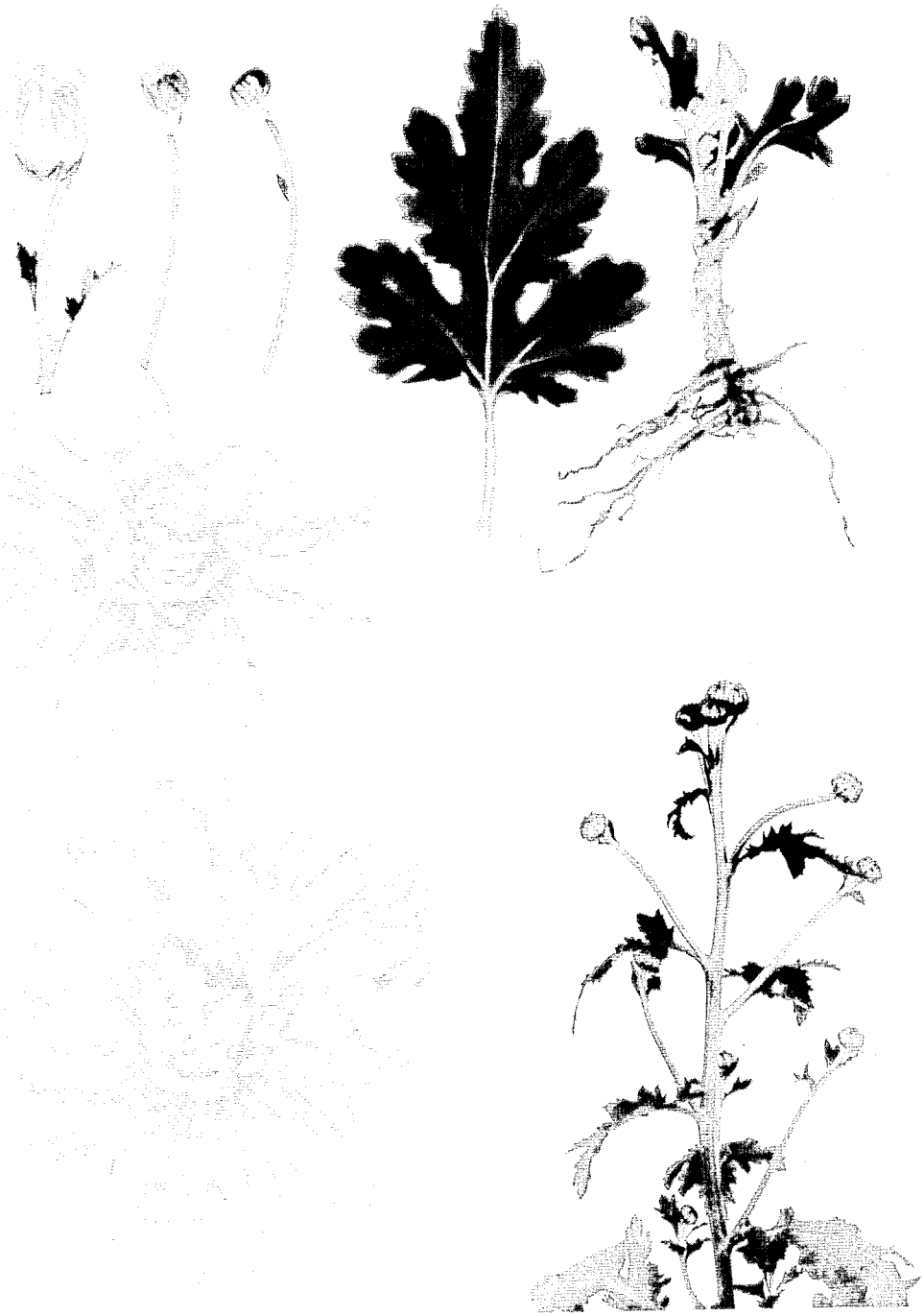
Inventor.
E. S. Boerner
By: Robb & Robb
Attorneys.

United States Patent Office

Plant Pat. 2,740
Patented May 16, 1967

2,740
CHRYSANTHEMUM PLANT

Eugene S. Boerner, Newark, N.Y., assignor to Jackson & Perkins Company, Newark, N.Y., a corporation of New York Filed May 11, 1966, Ser. No. 549,375
1 Claim. (Cl. Plt.—81)

The present invention relates to a new and distinct variety of chrysanthemum plant of the decorative class, which was originated by me by crossing an unnamed and unpatented large-flowered pink colored Hortorum seedling of unidentified parentage with the variety known as "Golden Cockatoo" (Plant Patent No. 1,638).

The primary objective of this breeding was to produce a new chrystanthemum variety which combines the flower color and wide petal form of the flowers of the unnamed pink seedling parent with the large flower size and strong habit of growth of the parent variety "Golden Cockatoo." This objective was fully achieved, as evidenced by the following unique combination of characteristics which are outstanding in the new variety and distinguish it from its parents, as well as from all other varieties of which I am aware:

(1) A strong habit of growth;
(2) A large flower size;
(3) A wide flower petal form; and
(4) A distinctive and attractive general color tonality of the flowers corresponding to Thulite Pink, lightly overcast with Cameo Pink.

Asexual reproduction of the new variety by both top cuttings and underground runners, as performed at Newark, N.Y., shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature:

Parentage: Seedling.
*Seed parent.*—An unnamed large-flowered pink Hortorum seedling.
*Pollen parent.*—"Golden Cockatoo."
Classification: Decorative.
Growth: Grows 24 inches tall.
Location where observations made: Outdoors at Newark, N.Y. in the early morning during the early part of the month of October.

Cold resistance: Winter hardy in northern New York State.
Blooming period: In Newark, N.Y. climatic area, bloom begins in early October and continues until frost.

*Flower*

Bud:
*Color.*—When petals first divide—Hellebore Red, Plate 38. When petals begin to unfurl—Thulite Pink, Plate 26, very lightly overcast with Spinel Pink, Plate 26. When half brown: inside—Thulite Pink, Plate 26, very lightly overcast with Rosolane Pink, Plate 26 in the center of the petal; outside—Rosolane Pink, Plate 26, lightly overcast with Cameo Pink, Plate 26.
*Peduncle.*—Color—Kildare Green, Plate 31. Strength—strong.

Bloom:
*Size.*—From 5½ to 6 inches.
*Stem.*—Stiff.
*Form.*—Decorative.
*Petalage.*—Double; wide petal.
*Color.*—Center of flower—Spinel Pink, Plate 26, with outer tip of petal overcast with Thulite Pink, Plate 26. Outer petals—Cameo Pink, Plate 26, lightly overcast with Thulite Pink, Plate 26. Base of petal—Glass Green, Plate 31. Inside of petal—Thulite Pink, Plate 26, lightly overcast with Cameo Pink, Plate 26. Reverse of petal—Cameo Pink, Plate 26.
*Petals.*—Texture—thick. Form—wide; oval.
*Fragrance.*—Characteristic chrysanthemum.

*Plant*

Form: Upright and branching.
Growth: Strong.
Foliage:
*Size.*—Large.
*Quantity.*—Normal.
*Color.*—Upper side—Dark Cress Green, Plate 31. Reverse side—Cress Green, Plate 31.
*Texture.*—Leathery.

I claim:

A new and distinct variety of chrystanthemum plant of the decorative class, substantially as herein shown and described, characterized particularly as to novelty by the unique combination of a strong habit of growth, a large flower size, a wide flower petal form, and a distinctive and attractive general color tonality of the flowers corresponding to Thulite Pink, lightly overcast with Cameo Pink.

No references cited.

ABRAHAM G. STONE, *Primary Examiner.*
ROBERT E. BAGWILL, *Examiner.*